United States Patent [19]

Klemps et al.

[11] Patent Number: 4,935,360

[45] Date of Patent: Jun. 19, 1990

[54] PROCESS FOR THE MICROBIAL ANAEROBIC PRODUCTION OF ACETIC ACID

[75] Inventors: Robert Klemps; Siegfried Schoberth; Hermann Sahm, all of Juelich; Werner Swyzen, Titz-Ameln, all of Fed. Rep. of Germany

[73] Assignees: Kernforschungsanlage Juelich GmbH, Juelich; Pfeifer Langen, Cologne, both of Fed. Rep. of Germany

[21] Appl. No.: 55,960

[22] Filed: Jun. 1, 1987

[30] Foreign Application Priority Data

Jun. 2, 1986 [DE] Fed. Rep. of Germany ........ 3718076

[51] Int. Cl.$^5$ ............................ C12P 7/54; C12R 1/02
[52] U.S. Cl. .................................... 435/140; 435/822; 435/823
[58] Field of Search .................... 435/140, 822 N, 823

[56] References Cited

U.S. PATENT DOCUMENTS

| | | | |
|---|---|---|---|
| 3,014,804 | 12/1961 | Els et al. ............................... | 435/140 |
| 3,779,868 | 12/1973 | Nikolaev et al. ..................... | 435/140 |
| 3,880,716 | 4/1975 | Engelbart et al. .................... | 435/140 |
| 4,022,665 | 5/1977 | Ghosh et al. ......................... | 435/140 |
| 4,076,844 | 2/1978 | Ebner et al. .......................... | 435/140 |
| 4,282,257 | 8/1981 | Kunimatsu et al. .................. | 435/140 |
| 4,371,619 | 2/1983 | Schwartz et al. ..................... | 435/140 |
| 4,378,375 | 3/1983 | Kunimatsv et al. .................. | 435/140 |
| 4,456,622 | 6/1984 | Maselli et al. ........................ | 435/140 |
| 4,506,012 | 3/1985 | Reed ..................................... | 435/140 |
| 4,687,668 | 8/1987 | Ghommidh et al. ................. | 435/140 |

FOREIGN PATENT DOCUMENTS

| | | | |
|---|---|---|---|
| 0120370 | 10/1984 | European Pat. Off. ............ | 435/140 |
| 3005099 | 8/1980 | Fed. Rep. of Germany ...... | 435/140 |
| 0044696 | 4/1978 | Japan .................................. | 435/140 |
| 0469746 | 5/1975 | U.S.S.R. ............................. | 435/140 |
| 1221327 | 4/1968 | United Kingdom . | |
| 1374302 | 11/1974 | United Kingdom ............... | 435/140 |
| 2125064 | 2/1984 | United Kingdom . | |

OTHER PUBLICATIONS

Abstract: Kikkoman Corp., JP 60133873.
Abstract, 95:76792s, Leigh et al., "Acetogenium Kivui, a New Thermophillic Hydrogen-Oxidizing Acetogenic Bacterium".
Sugaya et al., *Biotechnology and Bioengineering*, "Production of Acetic Acid by Clostridium Thermoaceticum in Batch and Continuous Fermentations", vol. XXVIII, pp. 678–683, (1986).
European Search Report, EP 87107859, (7-21-88).

*Primary Examiner*—Herbert J. Lilling
*Attorney, Agent, or Firm*—Foley & Lardner, Schwartz, Jeffery, Schwaab, Mack, Blumenthal & Evans

[57] ABSTRACT

An anaerobic production of acetic acid by fermentation can employ homoacetogenic bacteria in an aqueous solution of fermentable substrates, especially sugar, with the result of increased acetic-acid concentrations (over 3%), when the substrate solution initially used in the fermentation already contains acetic acid, for example, from a previous fermentation. In a fed-batch process, acetic acid is preferably present in a concentration ranging from about 0.5% to about 2%, and especially around 1%. At least two fermenters in compound (interconnected) arrangement are used. A real continuous fermentation is realized in at least two sequentially-operated fermenters by regulating the residence time in the first at about 1 day and in the second fermenter at at least 2 days.

31 Claims, 1 Drawing Sheet

PROCESS FOR THE MICROBIAL ANAEROBIC PRODUCTION OF ACETIC ACID

Background of the Invention

The present invention relates to a process for the anaerobic production of acetic acid from substrates for homoacetogenic bacteria, in particular from sugar solutions, by fermentation using homoacetogenic bacteria in an aqueous medium.

Acetic acid is a raw material of importance to the chemical industry that is required in increasing amounts and that is presently prepared, in large quantities, from petroleum and natural gas. Acetic acid can also be prepared by microbial conversion of sugars by (1) alcoholic fermentation and then (2) incomplete oxidation of the resulting ethanol by aerobic acetic-acid bacteria, as briefly outlined below:

$$C_6H_{12}O_6 \text{ (glucose)} \rightarrow 2\ CH_3CH_2OH + 2\ CO_2$$

$$2\ CH_3CH_2OH + 2\ O_2 \rightarrow 2\ CH_3COOH + 2\ H_2O.$$

In this two-step conversion of glucose into acetic acid, a maximum of 0.67 kg of acetic acid is formed per 1 kg of glucose, i.e., the maximum possible yield based on reacted glucose is only 67%. In contrast, it is possible using anaerobic homoacetogenic bacteria to convert sugars virtually quantitatively into acetic acid:

$$C_6H_{12}O_6 \rightarrow 3\ CH_3COOH.$$

The latter process is called "homoacetate fermentation." Bacteria that are "homoacetogenic," i.e., that live strictly anaerobically and are capable of converting glucose, fructose or xylose into acetic acid via homoacetogenic fermentation, have been known for some time. For example, a few strains of the genera Clostridium, Acetobacterium and Acetooenium, respectively, are able to convert not only sugars but also other low molecular weight compounds, such as lactate, pyruvate, carbon monoxide, formate, carbon dioxide and hydrogen, and methanol, into acetic acid.

The ability to carry out the quantitative conversion of sugars or other substrates into acetic acid in a single step, while dispensing with the introduction of oxygen into the bacterial suspension which is necessary in aerobic processes, makes homoacetate fermentation appear particularly favorable. But there is a considerable disadvantage in homoacetate fermentation presented by the sensitivity of known homoacetogenic bacteria to acetic acid, resulting in pronounced inhibition of acetic-acid formation as the concentration of the fermentation product increases.

It is normally impossible, therefore, to reach acetic acid concentrations above about 3.5%. The low acetic-acid contents achieved with conventional homoacetate fermentations processes have hindered the economical use of such processes.

Summary of the Invention

It is therefore an object of the present invention to provide a process for the production of acetic acid whereby higher acid concentrations, preferably in the range of 4% to 5%, are effected by homoacetate fermentation.

This object is achieved by a microbial fermentation process, according to the present invention, wherein the fermentation is carried out with acetic acid being present initially, in a fed batch process or, operating continuously in at least two successive fermenters. The acid is present, at least in part, in the form of acetate, as the medium is at a pH between 5 and 7.5.

More specifically, there has been provided, in accordance with one aspect of the present invention, a process for the anaerobic production of acetic acid by homoacetate fermentation, comprising the steps of (1) providing an aqueous fermentation medium comprising acetic acid and a substrate suitable for homoacetogenic bacteria; and (2) bringing the substrate in the fermentation medium into contact with microbes of at least one homoacetogenic bacterial strain, such that there is a conversion of the substrate into acetic acid by the fermentative action of the microbes, wherein (a) the conversion takes place in at least two fermenters in an arrangement comprised of a first fermenter and a second fermenter, there being a transferal of at least a part of the contents of the first fermenter into the second fermenter while the microbes are still active; and (b) the substrate-to-acetic-acid conversion is completed in at least one of said fermenters, the other fermenter being resupplied with the substrate-containing fermentation medium.

In a preferred embodiment, the aforesaid conversion is carried out in two concurrently operating fermenters in a fed-batch process, such that, each time before a final acetic acid concentration is achieved in a fermenter (i) of these fermenters, a portion of its contents is transferred to the other fermenter (ii) as a starting culture, resulting in an acetate ion concentration of between 0.5 and 2% in fermenter (ii) after fermenter (ii) is replenished with fermentation medium. In another preferred embodiment, the conversion is effected via continuous fermentation within first and second fermenters connected in sequence, the residence time in the second fermenter being at least equal to the residence time in the first fermenter. In yet another preferred embodiment, the substrate used for the conversion, as described above, comprises biomass that is immobilized in at least one of the fermenters.

Other objects, features and advantages of the present invention will become apparent from the following detailed description. It should be understood, however, that the detailed description and the specific example, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 presents schematic representations of different process embodiments of the present invention. More specifically.

Detailed Description of Preferred Embodiments

Figure 1A:
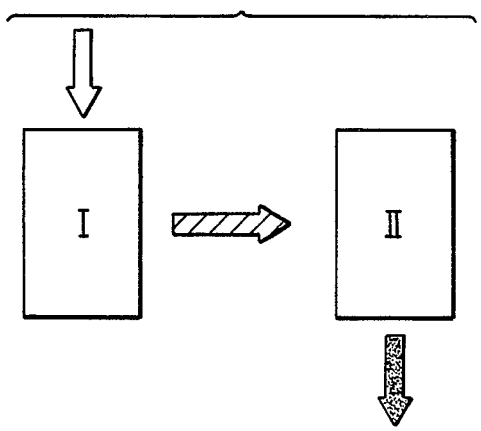
FIG. 1(a) shows two rectangles, "I" and "II", representing first and second fermenters, respectively. The striped arrow represents transfer of fermentation medium from fermenter I to fermenter II for final fermentation. The unshaded arrow represents additions of fresh, substrate-containing fermentation medium. The shaded arrow represents removal of medium after final fermentation.
Figure 1B:
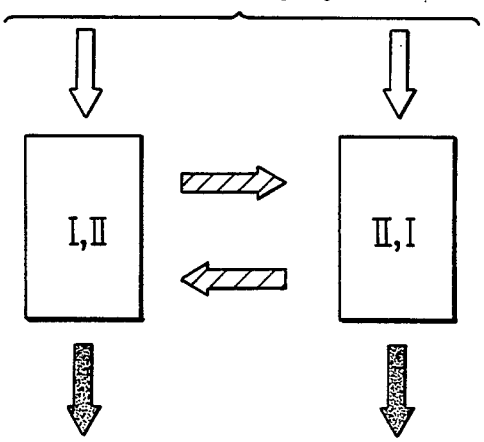
In FIG. 1(b), the two fermenters alternate as first and second fermenters.
Figure 1C:
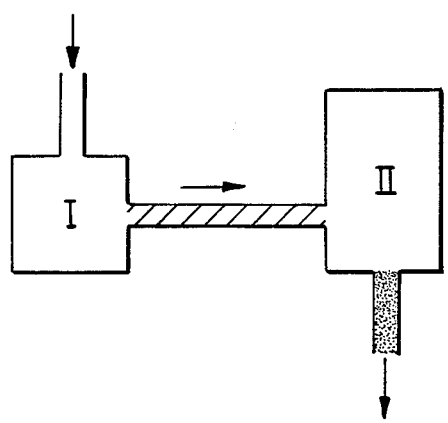
FIG. 1(c) depicts an arrangement wherein two fermenters I and II are physically connected, I being smaller than II.

In accordance with the present invention, a fermentation procedure takes place in at least two fermenters in compound arrangement, that is, in an arrangement where two or more separate fermenters are connected so as to permit the transfer of fermenter contents therebetween. More specifically, such a fermentation procedure can be realized in one of the following ways, pursuant to the present invention:

(a) In an arrangement comprising a first (I) and a second (II) fermenter, a portion of the fermentation liquid, representing between 20% and 80% of the total volume of the liquid, is repeatedly transferred to the second fermenter (II) each time a specific acetate concentration (for example, 3%) is achieved in the first fermenter (I), all while the microbes are still active. New substrate-containing fermentation medium is then supplied to the first fermenter (I), replenishing it, while the portion transferred to the second fermenter (II) is left there for final fermentation. Upon transferal of a portion, of liquid from the first fermenter (I) to the second (II), and a replenishing of the first fermenter (I), the resulting acetate ion concentration in the first fermenter (I) should be in the range of about 0.5% to 2%, preferably about 1%. When fermentation is carried out using *Acetogenium kivui*, it is preferable that the transfer be effected each time about 35 to 55 hours after replenishing and the starting of the fermentation in the first fermenter (I).

(b) According to another preferred embodiment, two fermenters, preferably of equal capacity, are operated concurrently in a fed-batch process, i.e., each operates in effect as a "first" fermenter. According to this procedure, each time before a final acetic acid concentration is achieved, and while the microbes are still active in a first one of these fermenters (I), a portion of the contents of the first fermenter (I) is transferred to the other (second) fermenter (II) as a starting culture, resulting in an acetate ion concentration of between about 0.5% and 2%, especially about 1%, in the second fermenter (II) after it is replenished with fresh fermentation medium. The remaining portion of fermentation medium in the first fermenter (I) is left therein for completing fermentation, whereafter the first fermenter (I) is emptied and prepared for use as the "second" fermenter (II) in a new cycle.

(c) Another preferred embodiment is illustrated by a real continuous procedure involving at least two fermenters (I and II, respectively) connected in sequence, the first of which being supplied with fermentation medium that contains substrate to be converted and the second one of which receiving the output of the first one. The capacity of these two fermenters are adapted to one another in a manner such that the residence time in the second fermenter in the sequence is at least equal to that in the first one, and is preferably at least twice, and especially three times, that of the first fermenter. The residence time in the first fermenter is thus selected so that an acetate ion concentration is obtained therein that is as high as possible but is compatible with the need for still-active microbes in the second fermenter (II), which receives its supply from the first one (I); the contents of the second fermenter (II) is subjected to subsequent fermentation until the final acetate concentration and low-glucose (substrate) residue is obtained. Preferably, the residence time in the first fermenter (I) is selected so that acetate-ion concentrations of about 3% are obtained in the first fermenter (I).

It has been found, surprisingly, that any one of procedures (a) to (c), according to the present invention, yields acetic acid or acetate concentrations above 4%, while either a simple fedbatch procedure or a continuous fermentation in only one fermenter results in concentrations not above 3.7%.

A fermentation pursuant to the present invention can be achieved by the use of a homoacetogenic bacterial species, as mentioned above. Further examples of such species can be found, e.g., in MICROBIAL METABOLISM, by G. Gottschalk (2d ed. 1985) (Springer NY), at page 250. Of these, *Acetogenium kivui* has proved particularly suitable in the present invention. *Acetoenium kivui* is an asporogenic, strictly anaerobic, Gram-negative, rod-shaped bacterium which shows optimal growth at a pH of 6.4 and temperature of 66° C. *Acetooenium kivui* also displays, in the context of the present invention, a surprisingly high rate of product formation and especially rapid growth. These properties are highlighted in Table 1, which presents data on acetic-acid formation, pursuant to the present invention, by the use of *A. kivui* (ATCC 33488/DSM 2030) and two other homoacetogenic bacteria, *Acetobacterium woodii* (ATCC 29683/DSM 1030) and *Clostridium thermoaceticum* (DSM 521). Other known strains of homoacetogenic bacteria can also be employed in this context.

TABLE 1

Formation of acetic acid from glucose by *A. woodii* (1), *Cl. thermoaceticum* (2) and *A. kivui* (3)

| Strain | Optimum temp. (°C.) | Prod. conc. (mmol % | Product formation rate (mmol/l · h) | Prod. yield (% gluc. reacted) | Cell activ. (nmol acetate/ min. mg prot.) |
|---|---|---|---|---|---|
| 1 | 33 | 133 | 0.7–1.3 | about 80 | 20 |
| 2 | 57 | 610 | 7–12 | more than 90 | 120 |
| 3 | 66 | 640 | 25–28 | 85–90 | 800 |

Mutants with enhanced productivity can be obtained, by using metagenic agents in a conventional manner, from the known homoacetogenic bacteria exemplified by the above-mentioned strains. It is also possible via known methods of genetic engineering to increase gene number or the efficiency of the appropriate promotor system to obtain strains characterized by higher production rates.

When *A. kivui* is used according to the present invention, the fermentation medium should contain an especially high concentration of trace elements (about 2- to 5-times), and an especially low concentration of phosphate (about 1/5 to 1/10), relative to the corresponding concentration values hitherto mentioned, respectively, in the literature for acetic acid production.

When *A. kivui* is used in a fermentation according to embodiment (b) of the present invention, moreover, a portion representing about 25% of the contents of the first fermenter is transferred into the second fermenter, typically about 36 to 42 hours after filling and starting the first fermenter. The second fermenter then receives (or may be just filled with) fresh fermentation medium to about 75% of that fermenter's volume. Fermentation is then started in the second fermenter, while the remaining portion in the first fermenter is left until the desired final concentration of acetate ions and low glucose (or substrate residue) is achieved, generally some 50 to 60 hours after the fermenter is filled and fermentation is started. The first fermenter is thereafter emptied and refilled to about 75% of its volume with fresh fermentation medium, whence it becomes the other (second) fermenter of the next cycle.

When a fermentation according to embodiments (a) or (b) is carried out, the whole amount of substrate, and especially glucose, to be converted can be contained in the fermentation medium as initially supplied. Alternatively, the initial fermentation medium can contain a lower starting concentration of glucose, preferably below 4% and especially of about 2% (±0.4%); glucose is then gradually supplied as fermentation proceeds, until the whole amount to be converted is added.

When a continuous fermentation is carried out in at least two sequentially-operated fermenters, the contents of which are pH-controlled by the adding of a neutralizing medium, e.g., 10 M NaOH, and *A. kivui* is used as homoacetogenic bacterial species, favorable results are obtained by selecting a residence time in the first fermenter of between about 18 and 24 hours, and a capacity ratio of 1:3 between the first and the second fermenter.

Any substrate, especially sugar, that is convertible by homoacetogenic bacteria used in the process of the present invention can be supplied to the fermentation, which preferably operates at temperatures in the range of 30° to 75° C. and at a pH in the range of 5 to 7.5, but even down to pH 3 when suitable, newly-isolated bacteria or bacteria produced by genetic engineering are used. The fermentation can be carried out with growing or with nongrowing (resting) cells, respectively. Preferably, the microbes are immobilized in the fermenter or separated from its output and recycled, since accumulated biomass shortens the fermentation time, e.g., by one-third with a 10x higher biomass concentration.

For the initial starting of the fermentation according to embodiments (a) or (b), an inoculum is preferably prepared separately, using a nutrient containing about 0.5% to 2% acetate and a substrate supplied immediately or gradually, until a total amount of acetic acid or acetate of more than 4% is obtained in the culture.

When *A. kivui* is used, the pH should be between 6.2 and 6.8 and the temperature between 60 and 70° C., and the supplied nutrient medium should contain 0.5% to 2% acetate ions. The nutrient medium can include all glucose that is to be converted; alternatively, glucose can be supplied gradually so as to maintain its concentration below 4%, preferably about 2%, until a total amount of 40 g/l of glucose are added during culture or fermentation. The fermentation is preferably carried out until a total concentration of more than 4% acetic acid or acetate results. The starting nutrient preferably contains 170 mM acetate, especially sodium acetate, and the preferred temperature and pH is about 66° C. and about 6.4, respectively, the latter value being controlled, e.g., by supplying 10 M NaOH solution. Of course, any other neutralizing medium, with any suitable concentration of neutralizing agent, can be used in this regard.

The present invention is further described by reference to the following illustrative examples.

Example 1.

1.1 Inoculum culture: The nutrient solution differed from the composition described below in 1.2 as follows: 7 g/l $K_2HPO_4$; 5,5 g/l $KH_2PO_4$; 2 g/l yeast extract; 0,5 g/l $(NH_4)_2SO_4$; 1 g/l NaCl and 0,5 g/l KCl; Tryptone being absent and 10 g/l $NaHCO_3$ being additionally added. The glucose concentration was 2% (w/v).

The nutrient solution was filled without free space in 100 ml vials with screw caps. The contents of an ampoule containing freeze-dried *A. kivui* was suspended in 2 ml of the nutrient solution, transferred into one of the nutrient solution-containing vials, and incubated at 66° C. Usually the turbidity of the culture ($OD_{660}$) was above 2 after 34 to 36 hours. Then 10% of this active culture gas inoculated into a fresh nutrient solution. After about 10 hours incubation at 66° C., the turbidity again was above 2 and that culture could be used as inoculum for the fermentation (1.2).

| 1.2 A nutrient solution of the following composition was placed in a 2-liter fermenter: | |
|---|---|
| $H_2O$ (double-distilled) | 1.01 l |
| Yeast extract (Merck), | 5.0 g |
| Tryptone (BBL 11921) | 3.0 g |
| $(NH_4)_2SO_4$ | 2.0 g |
| $MgSO_4 \times 2H_2O$ | 0.2 g |
| $CaCl_2\, 2H_2O$ | 0.15 g |
| KCl | 0.5 g |
| NaCl | 1.0 g |
| $KH_2PO_4$ | 1.5 g |
| $K_2HPO_4$ | 1.5 g |
| $NiCl_2$ (1 mM) | 1.3 ml |
| SeWo solution* | 0.6 ml |
| $Co(NO_3)_2 \times 6H_2O$ (0.1 M) | 1.1 ml |
| $(NH_4)_2 Fe(SO_4)_2$ (0.1 M) | 1.2 ml |
| $Na_2MoO_4 \times 2H_2O$ (0.1 M) | 1.1 ml |
| SL 9** | 1.2 ml |
| $Na_2S$ (0.5 M) | 2.0 ml |
| [Depending on the desired concentration, glucose was added as a concentrated solution] | |
| pH | 6.4 |
| temperature | 66°–68° C. |
| *SeWo solution | |
| $Na_2SeO_3 \times 5H_2O$ | 3 mg/l |
| $Na_2WoO_4 \times 2H_2O$ | 4 mg/l |
| **SL 9 | |
| $H_2O$, double-distilled | 1000 ml |
| Nitrilotriacetic acid (NTA) | 12.5 g |
| $FeCl_2 \times 4H_2O$ | 2.0 g |
| $ZnCl_2$ | 70 mg |
| $MnCl_2 \times 4H_2O$ | 100 mg |
| $H_3BO_3$ | 6 mg |
| $CoCl_2 \times 6H_2O$ | 190 mg |
| $CuCl_2 \times 2H_2O$ | 2 mg |
| $NiCl_2 \times 6H_2O$ | 24 mg |
| $Na_2MoO_4 \times 2H_2O$ | 36 mg |

About 170 mmol/l sodium acetate were added to this, as was 2% glucose, and the fermentation broth was inoculated with cells of *A. kivui* from a preculture (10% v/v inoculum). After 20 hours, a further addition of about 1.7% glucose to the fermenter was carried out. After a total of about 40 to 50 hours, the total concentration of acetic acid in the fermenter was about 4.3 to 4.6%.

A sufficient bacterial suspension was then transferred under sterile conditions from this fermenter into a second fermenter, which was filled with fresh nutrient solution, for the acetic acid concentration in the second fermenter to be about 0.8 to 1%. After about 50 hours, about 3.4 to 3.6% acetic acid had once again been formed, with a total concentration of 3.9 to 4.4% acetic acid being achieved (see Table 2 below).

It was possible to repeat this procedure in each case without loss of activity of the bacteria. Consequently, a 4-to-4.5% strength acetic acid solution, comprising about 75% of the fermenter volume, was produced after each cycle in about 50 hours.

In accordance with the present invention, the isolation and purification of acetic acid from the culture medium can be carried out by conventional methods.

TABLE 2

Results of test fermentations with *A. kivui*.*

| Fermenter Run No. | Initial amount Na acetate (mM) | Total amt. of acetic acid (mM %) | | Net amt. (mM) | Time (h) | Max. OD$_{660}$ | Hours before transf. |
|---|---|---|---|---|---|---|---|
| 1 | 158 | 744 | 4.4 | 586 | 48.0 | 8.5 | 31 |
| 2 | 80 | 644 | 3.9 | 564 | 41.5 | 8.9 | 41.5 |
| 3 | 100 | 669 | 4.0 | 569 | 49.5 | 9.1 | 49.5 |
| 4 | 78 | 693 | 4.2 | 615 | 46.5 | 9.0 | 46.5 |
| 5 | 130 | 730 | 4.3 | 600 | 57.0 | 8.9 | 50.0 |
| 6 | 170 | 690 | 4.1 | 520 | 49.5 | 8.3 | stopped |

*158 mM Na acetate was initially present in Run No. 1. The fermenter cells were then transferred after 31 hours to a new fermenter; the same thing happened with all the subsequent runs of the fermenter which are detailed.

The concurrent operation in two parallel-connected fermenters, as described above, could be varied by changing the 3:1 proportion of fermentation medium to fermentation broth containing acetic acid, considering the acetic acid concentration of the broth, up to a proportion of about 9 : 1, provided that the initial concentration of acetic acid or acetate in the fermentation medium was at least 0.5%.

Example 2.

The procedure of Example 1 was repeated without problems in a 10-liter measure with at least equally favorable results.

Table 3 shows these results when the initial acetic acid or acetate concentration was always about 1% and *A. kivui* was used at 66°-68° C. In addition 20-25% of the contents of one fermenter was transferred, as inoculum, to the next fermenter.

TABLE 3

| Fermenter-run No. | Final acetate conc. (%) | After (hours) | Time until transfer (hours) |
|---|---|---|---|
| 1 | 4,8 | 64 | 41 |
| 2 | 4,2 | 70,5 | 36 |
| 3 | 4,6 | 60 | 44 |
| 4 | 3,9 | 68 | 43,5 |
| 5 | 4,2 | 48 | stopped |

Example 3.

Results of a real continuous production in two sequentially-operated fermenters of 1-liter and 3-liter capacity, respectively, are shown in Table 4.

TABLE 4

|  | Fermenter 1 | Fermenter 2 |
|---|---|---|
| Residence time (h) | 21 | 63 |
| Turbidity (OD 660 nm) | 9.5 | 8.2 |
| Acetic acid (%) | 3 | 4.1 |
| (mM) | 500 | 679 |
| Residual glucose (%) | 1.24 | 0.04 |
| (mM) | 69.12 | 2.16 |
| Bacterial Protein (mg/l) | 1113 | 978 |

Comparable conversions as described above could be carried out using other homoacetogenic bacterial species, thereby obtaining favorable results in comparison with those achieved via conventional techniques.

The concentration range of acetate ions in the fermentation medium, when one is restarting the fermentation of a fed batch process (a) or (b), is not limited to 0.5-to-2%. Instead, a broader range of 0.3% to 6% can be employed with other strains of homoactogenic bacteria, including those strains produced by genetic engineering that are able to produce especially high amounts of acetic acid.

What is claimed is:

1. A process for the anaerobic production of acetic acid by homoacetate fermentation, comprising the steps of
    (1) providing an aqueous fermentation medium in a first fermenter, said fermentation medium comprising a sugar suitable for fermentation by a homoacetogenic bacterial strain to achieve a final acetate ion concentration range; and
    (2) adding at least said bacterial strain to said first fermenter to initiate a cycle under conditions such that said bacterial strain converts sugar in said fermentation medium into acetic acid or acetate ion, said process occurring in a plurality of fermenters, said plurality comprising at least a first fermenter and a second fermenter, and said cycle comprising the following steps:
    (A) after a first fermentation time of 36 to 42 hours, based on a time of 50 to 60 hours to achieve said final acetate ion concentration range in said first fermenter, transferring a portion A of the contents of said first fermenter, said contents comprising said portion A and a portion B, into said second fermenter, leaving portion B in said first fermenter, wherein portions A and B differ in volume; then
    (B) replenishing the fermenter that contains the smaller of portions A and B with fresh fermentation medium, such that the acetate ion concentration in said fermenter is between 0.5% and 2.0% (w/v); and
    (C) after a second fermentation time representing the time necessary to achieve said final acetate ion concentration range in the fermenter that contains the larger portion of portions A and B, removing the contents of said fermenter which received said larger portion.

2. A process according to claim 1, wherein said fermentation is carried out with *Acetogenium kivui*, at a pH of between 6.2 and 6.8 and at a temperature of between 60° and 70° C., in a fermentation medium containing about 0.5% to 2% acetate ions, and wherein glucose is gradually supplied to maintain a glucose concentration in said fermentation medium that is below 4% until a total concentration of acetate ions of more than 4% is achieved.

3. A process according to claim 1, wherein said fermentation medium has an initial acetate ion concentration of between about 0.5% and 2%, and said final acetate ion concentration is at least 4%.

4. A process according to claim 1, wherein a concentration of said sugar is maintained at about 2% during said fermentation, and said sugar is supplied until about 40 g/l of glucose are added.

5. A process according to claim 1, wherein said fermentation is carried out at about pH 6.4 and around 66° C., and wherein said nutrient medium has an initial acetate concentration of about 170 mmol/l.

6. A process according to claim 1, wherein said starting acetate concentration is comprised of sodium acetate, and wherein pH regulation is accomplished by supplying an approximately 10 M sodium hydroxide solution.

7. A process according to claim 1, wherein said bacterial strain is of the species *Acetogenium kivui*.

8. A process according to claim 7, wherein said sugar comprises glucose and the total amount of said glucose to be converted is gradually supplied, as fermentation proceeds, until said total amount of glucose to be converted is added.

9. A process according to claim 8, wherein the gradual supply of glucose is controlled such that a glucose concentrations of about 2% is maintained in the contents of said first fermenter and at least said second fermenter until about 40 g/l of glucose are added.

10. A process according to claim 1, wherein a first inoculum for initiating fermentation is obtained by cultivating a homoacetogenic bacterial strain in a nutrient medium, said nutrient medium having an initial acetate ion concentration of between about 0.5 to 2%, until said nutrient medium has a total acetate ion concentration of more than 4%.

11. A process according to claim 1, wherein said bacteria of said bacterial strain are separated from contents removed from said fermenters and recycled.

12. A process according to claim 11, wherein said concentration is above 4%.

13. A process for the anaerobic production of acetic acid by continuous homoacetate fermentation, comprising the steps of
(A) providing an aqueous fermentation medium in a first fermenter, said fermentation medium comprising a sugar suitable for fermentation by a homoacetogenic bacterial strain to achieve a final acetate ion concentration range;
(B) adding said bacterial strain to said first fermenter to initiate said continuous fermentation under conditions such that said bacterial strain converts sugar in said fermentation medium into acetic acid or acetate ion, said process occurring in a plurality of fermenters, connected in sequence, that comprises at least said first fermenter and a second fermenter; and
(C) continuously (i) transferring a portion of the contents of said first fermenter from said first fermenter into said second fermenter, (ii) continuously replenishing said first fermenter with a fresh fermentation medium and (iii) continuously discharging a product solution from said second fermenter, wherein (1) a fermentation time of fermentation medium in said first fermenter is sufficient to obtain an acetate ion concentration of about 3% in said first fermenter and (2) a fermentation time of fermentation medium in said second fermenter is at least equal to the fermentation time of fermentation medium in said first fermenter.

14. A process according to claim 13, wherein
(1) said conversion is effected via a continuous fermentation;
(2) said first and second fermenters are connected in sequence; and
(3) the fermentation time of fermentation medium in said second fermenter is about three times longer than the fermentation time of fermentation medium in the first fermenter.

15. A process according to claim 13, wherein said fermentation time in said first fermenter is between 18 and 24 hours, and said fermentation time in said second fermenter is between 54 and 75 hours.

16. A process according to claim 13, wherein said first fermenter has a capacity that is related to the capacity of at least said fermenter in a ratio ranging between about 1:1 and about 1:3.

17. A process according to claim 13, wherein said second fermentation time in said second fermenter is at least twice the length of said first fermentation time in said first fermenter.

18. A process according to claim 17, wherein said second fermentation time in said second fermenter is at least three times the length of said first fermentation time in said first fermenter.

19. A process according to claim 1, wherein said smaller portion, in step (B) is about 25%, and said fresh fermentation medium occupies about 75% of the volume of said one fermenter or said other fermenter.

20. A process according to claim 7, wherein said first fermentation time in step (A) is about 36 to 42 hours in length, and wherein said second fermentation time in step (C) is about 50 to 60 hours after said replenishing.

21. A process according to claim 1, wherein said acetate ion concentration is about 1% after said replenishing.

22. A process according to claim 13, wherein said bacterial strain is of the species *Acetogenium kivui*.

23. A process according to claim 22, wherein said fermentation time in said fermentation medium in said first fermenter in step (C) (iii) is about 18 to 24 hours in length, and wherein said fermentation time in said fermentation medium in said second fermenter in step (C) (iii) is about 54 to 75 hours after said replenishing.

24. A process according to claim 13, wherein said sugar comprises glucose and the total amount of said glucose to be converted is gradually supplied, as fermentation proceeds, until said total amount of glucose to be converted is added.

25. A process according to claim 13, wherein said bacteria of said bacterial strain are separated from the contents removed from said fermenters and recycled in said process.

26. A process according to claim 13, wherein said fermentation is carried out with *Acetogenium kivui*, at a pH of between 6.2 and 6.8 and at a temperature of between 60° and 70° C., in a fermentation medium containing about 0.5% to 2% acetate ions, and wherein glucose is gradually supplied to maintain a glucose concentration in said fermentation medium that is below 4% until a total concentration of acetate ions of more than 4% is achieved.

27. A process according to claim 13, wherein said fermentation medium has an initial acetate ion concentration of between about 0.5% and 2%, and said final acetate ion concentration is at least 4%.

28. A process according to claim 13, wherein a concentration of said sugar is maintained at about 2% during said fermentation, and said sugar is supplied until about 40 g/l of glucose are added.

29. A process according to claim 13, wherein said fermentation is carried out at about pH 6.4 and around 66° C., and wherein said nutrient medium has an initial acetate concentration of about 170 mmol/l.

30. A process according to claim 13, wherein said starting acetate concentration is comprised of sodium acetate, and wherein pH regulation is accomplished by supplying an approximately 10 M sodium hydroxide solution.

31. A process for the anaerobic production of acetic acid by fed-batch homoacetate fermentation, comprising the steps of (A) providing an aqueous fermentation medium in a first fermenter, said fermentation medium comprising a sugar suitable for fermentation by a homoacetogenic bacterial strain to achieve a final concentration range of acetate ion; and (B) adding at least said bacterial strain to said first fermenter to initiate a cycle under conditions such that said bacterial strain converts sugar in said fermentation medium into acetic acid or acetate ion, said cycle comprising one of the following sets of steps:

FIRST SET OF STEPS (1) after a first time interval of 36 to 42 hours, based on a time of 50 to 60 hours to reach said final concentration range in said first fermenter, transferring a portion of the contents of said first fermenter into a second fermenter; then (2) adding fresh fermentation medium to said second fermenter until the acetate ion concentration therein is between 0.5% and 2.0% by volume;

(3) after a second time interval such that said final concentration range is achieved in said first fermenter, emptying said first fermenter;

(4) after a third time interval of 36 to 42 hours, based on a time of 50 to 60 hours to reach said final concentration range in said second fermenter, transferring a portion of the contents of said second fermenter into said first fermenter;

(5) adding fresh fermentation medium to said first fermenter until the acetate ion concentration therein is between 0.5% and 2.0% (w/v); and then (6) after a fourth time interval such that said final concentration range is achieved in said second fermenter, emptying said second fermenter, and

SECOND SET OF STEPS (1') after a first time interval of 36 to 42 hours, based on a time of 50 to 60 hours to reach said final concentration range in said first fermenter, transferring a portion of the contents of said first fermenter into a second fermenter; then (2') adding fresh fermentation medium to said first fermenter, until the acetate ion concentration in said first fermenter is between 0.5% and 2.0% (w/v) by volume; and thereafter (3') after a second time interval such that said final concentration range is achieved in said second fermenter, emptying said second fermenter.

* * * * *